(12) United States Patent
Kenney

(10) Patent No.: US 6,531,098 B1
(45) Date of Patent: Mar. 11, 2003

(54) DISPOSABLE PRESELECTED-VOLUME, CAPILLARY PIPETTE DEVICE HAVING AN INTEGRALLY-FORMED BULBOUS END AND METHOD OF TAKING BLOOD SAMPLES USING THE DEVICE

(75) Inventor: James W Kenney, Broomall, PA (US)

(73) Assignee: Drummond Scientific Company, Broomall, PA (US)

( * ) Notice: Subject to any disclaimer, the term of this patent is extended or adjusted under 35 U.S.C. 154(b) by 0 days.

(21) Appl. No.: 09/183,934

(22) Filed: Oct. 30, 1998

Related U.S. Application Data

(60) Provisional application No. 60/105,658, filed on Oct. 26, 1998.

(51) Int. Cl.$^7$ .................................................. B01L 3/02
(52) U.S. Cl. ..................... 422/100; 422/102; 436/180; 73/864.11; 222/209
(58) Field of Search ............................... 422/58.61, 102, 422/100; 73/863.32, 863.81, 864.11; 222/420, 209; 436/180

(56) References Cited

U.S. PATENT DOCUMENTS

| | | | | |
|---|---|---|---|---|
| 4,212,204 A | * | 7/1980 | St. Amand | 422/100 |
| 4,963,498 A | * | 10/1990 | Hillman et al. | 422/102 |
| 5,409,664 A | * | 4/1995 | Allen | 422/58 |
| 5,460,782 A | * | 10/1995 | Coleman et al. | 422/100 |
| 5,739,041 A | * | 4/1998 | Nazareth et al. | 422/58 |

* cited by examiner

*Primary Examiner*—Lyle A. Alexander
(74) *Attorney, Agent, or Firm*—Volpe and Koenig, P.C.

(57) ABSTRACT

The present invention relates to a disposable, preselected-volume, capillary pipette device for picking up and transferring a selected volume of a liquid sample such as blood.

17 Claims, 3 Drawing Sheets

DISPOSABLE PRESELECTED-VOLUME, CAPILLARY PIPETTE DEVICE HAVING AN INTEGRALLY-FORMED BULBOUS END AND METHOD OF TAKING BLOOD SAMPLES USING THE DEVICE

This application claims benefit of Provisional Application Ser. No. 60/105,658 filed Oct. 26, 1998.

FIELD OF THE INVENTION

The present invention relates to a disposable, preselected-volume, capillary pipette device for picking up and transferring a selected volume of a liquid sample such as blood. The present invention also provides a novel method of making and recalibrating the pipette device and using the device to take blood samples.

BACKGROUND OF THE INVENTION

Capillary pipette devices are well known for collecting blood samples from a patient who has been pricked with a needle to instigate blood flow ("finger stick"). Such disposable pipette devices are disclosed, for example, by Kenney in U.S. Pat. No. 5,059,398 and by Coleman et al. in U.S. Pat. No. 5,460,782, both of which are incorporated herein by reference. Coleman et al., U.S. Pat. No. 5,460,782 (hereinafter Coleman) discloses an automatic filling micropipette formed from a tubular body having an open end, and being closed or having a piston at the opposite end. The open end of the tubular body is sized to permit liquid to flow into the tubular body by capillary action. A vent hole 6 is positioned at a preselected point along the body of the tube to limit the amount of liquid which enters the tube by capillary action.

The device disclosed by Coleman is useful for collecting a sample of blood from a "finger stick." However, the embodiments illustrated in FIGS. 1–3, 5 and 6 of Coleman have multiple components which are costly to make and assemble to form the finished product. For example, in FIGS. 1–3, a flexible closed tube 4 and a sample collection tube 2 must be separately manufactured and assembled. In FIGS. 5 and 6, a plunger or piston 30 and a sample collection tube 22 must be separately manufactured and assembled. The cost of making and assembling these multi-component designs is prohibitively expensive. Therefore, it would be desirable to provide a single-component, preselected-volume pipetting device which is inexpensive to manufacture.

In FIG. 4, Coleman discloses a single-piece, preselected-volume micropipette formed from a single flexible tube 12. While this embodiment appears to be easier and less costly to manufacture than the embodiments disclosed in FIGS. 1–3 and 5–6, this embodiment does not function as well as the other embodiments disclosed by Coleman.

For example, referring to FIG. 4 of Coleman, liquid from the filled collection tube 12 is expelled by squeezing the proximal end 15 of the tube. Since the proximal end of the tube 15 is not bulbous, the volume of air contained therein may not be sufficient to emit the fluid sample with a single squeeze. Splatering of the liquid sample may occur if the proximal end must be squeezed repetatively to emit the sample.

Further, the reduced diameter of the proximal end of Coleman's tube 12 increases the tube's rigidity, thereby providing resistance to squeezing by a technician. Therefore, it would be desirable to provide a disposable, preselected-volume capillary pipette device formed from a single, contiguous tube of hydrophilic and elastomeric material having an elongate capillary section formed at one end of the tube and an enlarged diameter, bulbous section formed at the other end of the tube.

Forming a pipette device from a single, contiguous tube of elastomeric material using prior art techniques is difficult. For example, using blow molding to form the enlarged-diameter bulbous end of the tube is very difficult since elastomeric and hydrophilic materials, such as PEBAX and BAREX, change from a semi-rigid state to a fluid state within a very small temperature range (for example, 4° F. for PEBAX). Precise temperature and pressure control are required to insure the integrity of the product. Additionally, precision forming by blow molding is very difficult since the thickness of elastomeric tube stock has a large tolerance. Therefore, it would be desirable to provide an easy and efficient method of making a pipetting device having a bulbous end without blow molding an elastomeric and hydrophilic material such as PEBAX or BAREX.

Preselected-volume capillary pipetting devices must provided in a wide range of calibrated volumes. For example, a particular laboratory blood test may require any where from 5 to 150 microliters of blood from a "finger stick." Blow molding equipment requires timely reconfiguration to change the calibrated volume of the device. Therefore, it would also be desirable to provide a simple and inexpensive method of making preselected-volume capillary pipetting device in a wide variety of calibrated volumes.

SUMMARY OF THE INVENTION

The present invention provides a disposable, preselected-volume, capillary pipette device formed from a single, contiguous tube of hydrophilic and elastomeric material. The invention also provides an inexpensive and easy method of manufacturing and re-calibrating the pipette device within a wide range of volumes.

The disposable, preselected-volume, capillary pipette device is made of a single, contiguous, tube of hydrophilic and elastomeric material. The material preferably comprises a polyether block polyamide sold by Elf AtoChem under the trademark PEBAX or a wettable thermoplastic acrylonitrile barrier sold by Elf AtoChem under the trademark BAREX. The tube has a flexible wall and a channel extending from a first end to a second end. The tube has a thickness in the range of 5 to 7 mils (0.13 to 0.18 mm.).

The tube has a fluid flow port having a diameter D1 at the first end for admitting and emitting liquids to and from the tube. The fluid flow port has a diameter D1 in the range of 0.03 to 0.1 in. (0.08 to 0.25 cm.). The tube has a seal at the second end. The seal preferably comprises a heat seal.

A capillary section is formed at the first end of the tube. The capillary section extends a distance L1 from the fluid flow port to a preselected intermediate point on the tube. The channel has an inner diameter equal to D1 in the capillary section.

A bulbous section is formed at the second end of the tube. The bulbous section extends a distance L2 from the preselected intermediate point to the seal. The channel has an inner diameter D2 greater than D1 in the bulbous section. Preferably the channel has a diameter D2 in the range of 0.15 to 0.3 in. (0.38 to 0.76 cm.). Preferably, D2 is at least two or three times as large as D1.

A vent hole extends through the flexible wall in the capillary section of the tube. The vent hole has a diameter D3 smaller than D1. Preferably, the vent hole has a diameter in the range of 0.004 to 0.016 in. (0.01 to 0.04 cm.).

The vent hole is positioned in the tube at a preselected distance L3 from the port to define a liquid sample chamber within the capillary section. The liquid sample chamber has a preselected calibrated volume defined by the equation $\pi(D1/2)^2 L3$. The calibrated volume is preferably from 5 to 150 microliters. The calibrated volume is less than the volume of the bulbous section.

The device includes a pair of opposed fins fixed to and projecting radially-outwardly from the capillary section. The fins extends the entire length of the capillary section. The fins may include identifying indicia printed thereon. The method of making the pipetting device comprises the initial step of providing a contiguous, preselected length of hydrophilic and elastomeric tube having a first and second end, a flexible wall, and a constant inner diameter D2. The first end of the tube is then heat sealed.

The tube is bifurcated into a bulbous section proximate the first end and a capillary section proximate the second end. The inner diameter of the capillary section of the tube is reduced to a constant diameter D1. Preferably, the inner diameter is reduced by heating and crimping the capillary section to reduce the inner diameter of the capillary section to a diameter D1 less than D2. Prior to heat crimping, a cylindrical rod is inserted into the capillary section. The cylindrical rod has an outer diameter equal to the selected diameter D1. The capillary section is reshaped into an elongate, cylindrical tube having an inner diameter D1 and a pair of diametrically-opposed, radially projecting fins extending along the length of the capillary section.

A vent hole is drilled through the capillary section of the tube at a distance L3 from the port. The vent hole has a diameter D3 smaller than D1.

The fins are tapered proximate the second end of the capillary section of the tube. The fins are tapered by shearing in a direction generally along the length of the fins.

DESCRIPTION OF PREFERRED EMBODIMENTS

Figure 1:
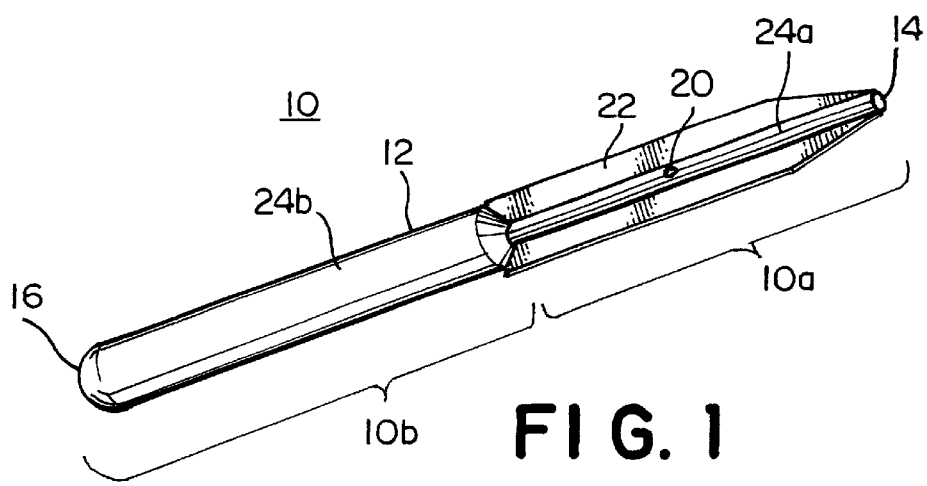
FIG. 1 is a perspective view of the pipetting device in accordance with an embodiment of the invention.

Preferred embodiments of the invention are described below with reference to FIGS. 1–10 wherein like reference numerals are used throughout to designate like elements.

Figure 2:
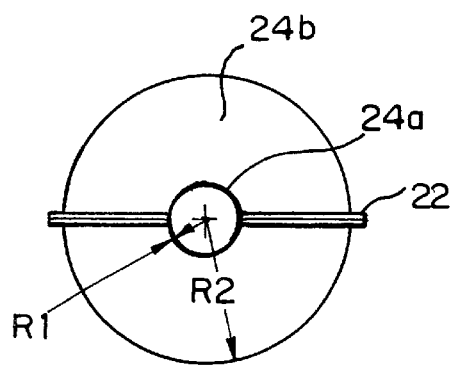
FIG. 2 is an end view of the pipetting device illustrated in FIG. 1.
Figure 3:
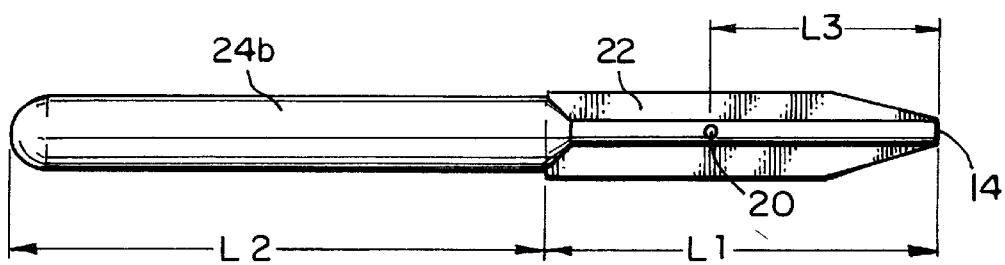
FIG. 3 is a top plan view of the pipetting device illustrated in FIG. 1.

A disposable, preselected-volume, capillary pipette device, designated generally by reference numeral 10, is illustrated in FIGS. 1–3. The pipette device 10 is formed from a single, contiguous, tube of material which is both hydrophilic and elastomeric. Preferably, the pipetting device is made of a polyether block polyamide such as is sold by Elf AtoChem under the trademark PEBAX 6333. The pipetting device may also be made of a wettable thermoplastic acrylonitrile barrier such as is sold by Elf AtoChem under the trademark BAREX. Other known hydrophilic and elastomeric materials may also be used. The tube 12 has a flexible wall having a thickness in the range of 5 to 7 mils (0.13 to 0.18 mm.), preferably about 6 mils (0.15 mm).

The device 10 is bifurcated into two sections, a capillary section 10a and a bulbous section 10b. The capillary section 10a is calibrated to collect a preselected volume of a liquid sample such as blood. The liquid sample contained in the capillary section 10a can then be expelled by squeezing the bulbous section 10b of the device. The volume of the bulbous section 10b is much greater than the calibrated volume of the capillary section 10a so that the entire liquid sample is expelled by gently squeezing the bulbous section 10b a single time with the thumb and index finger.

A central channel 24 extends along the entire length of the tube 12. The channel 24 has an enlarged diameter D2 in the bulbous section 10b of the tube and a reduced diameter D1 in the capillary section of the tube. The channel 24 tapers from the D2 to D1 at an intermediate point on the tube. The reduction in diameter from D2 to D1 is formed by heated crimping, described in detail below.

The inner diameter of the channel in the capillary section and bulbous section are selected based on the desired calibrated volume of the device 10. The device 10 has particular use for collecting a sample of blood from 5 to 150 microliters from a "finger stick." Accordingly, the inner diameter D2 of the channel in the bulbous section may range from 0.15 to 0.3 in. (0.38 to 0.76 cm.) while the inner diameter D1 of the channel in the capillary section may range from 0.03 to 0.1 in. (0.8 to 0.25 cm.) depending on the desired calibrated volume of the device 10.

The tube 12 has an open port 14 at one end for admitting and emitting the fluid sample. The diameter D1 of the port is the same as the diameter of the fluid channel in the capillary section 10a. The diameter D1 of the port is also determined in part by the selected calibrated volume of the capillary section 10b.

The tube 12 is sealed at the other end. The seal 16 is preferably a heat seal but may also be a plug or other seal material.

A vent hole 20 is formed in the capillary section and extends entirely through the tube wall. The vent hole 20 has a diameter D3 which is much smaller than the diameter of the capillary section D1. In the embodiment illustrated in FIGS. 1–3, the vent hole diameter D3 is 0.004 to 0.016 in. (0.01 to 0.04 cm.). The vent hole 20 is large enough to allow air to vent from the tube 12 during capillary attraction of a liquid sample into the device 10, but small emough to prevent the liquid sample from escaping the tube once the liquid sample reaches the vent hole.

The vent hole 20 can be located at any lengthwise location in the capillary section 10a. The longitudinal location of the vent hole 20 limits the distance the fluid sample will be drawn into the capillary section 10a of the tube 12. Once the liquid reaches the vent hole 20, no further liquid is drawn into the device. Therefore, the longitidinal location of the vent hole 20, and the diameter D1 of the capillary tube, determine the calibrated volume of the device 10.

The calibrated volume of the device is equal to the volume of the channel between the vent hole 20 and the port 14. Referring to FIGS. 2 and 3, the calibrated volume of the capillary tube is equal to $\pi R1^2 L3$. The dimensions of working examples of the device 10 are presented below in Table I.

TABLE I

| Nominal calibrated volume (ul) | Vent hole length L3 (cm) | Capillary section length L1 (cm) | Capillary section diameter D1 (cm) D1 | Bulbous section length L2 (cm) | Bulbous section diameter D2 (cm) |
|---|---|---|---|---|---|
| 18 | 1.7 | 3.01 | 0.117 | 2.515 | 0.394 |
| 39 | 1.7 | 3.01 | 0.173 | 2.515 | 0.394 |
| 98 | 2.0 | 3.01 | 0.25 | 2.515 | 0.394 |
| 123 | 2.5 | 3.01 | 0.25 | 2.515 | 0.394 |

The channel 24a in the capillary section 10a has a diameter equal to D1 which is much smaller than the diameter of the channel 24b in the bulbous section 10b. The diameter D1 will vary depending on the preselected volume of the pipetting device 10. For devices 10 having a calibrated sampling volume less than 30 microliters, D1 is preferably equal to 0.046 in. (0.117 cm.). For pipetting devices 10 having a calibrated sampling volume from 30 to 65 microliters, D1 is preferably equal to 0.068 in. (0.173 cm.). For devices 10 having a calibrated volume greater than 65 microliters, D1 is preferably equal to 0.1 in. (0.25 cm.).

A pair of diametrically-opposed fins 22 are integrally formed with and extend radially from the capillary section 10a of the tube. The fins 22 extend along the entire length of the capillary section 10a of the tube 12. The fins 22 are a by-product of the novel method of making the device 10, described below, from a single piece of tube. The fins 22 add rigidity and support to the capillary section 10a of the tube. The fins 22 also provide a flat surface onto which printing or color coding may be applied for device identification. For example, the capacity (volume) of the device 10 or identity of the liquid sample may be printed on the fins 22. The fins 22 are tapered near the port 14 so that the liquid sample does not contact and become attracted to the outside of the fins during sampling.

Liquid sampling is accomplished by simply touching the port end of the device 10 to the liquid sample. The liquid sample is automatically drawn by capillary action into the capillary section 18a of the tube. The liquid sample is emitted from the device 10 by squeezing the bulbous section 18b of the tube. Since the volume of the bulbous section 10b is much greater than the calibrated volume, the entire liquid sample is emitted from the tube by squeezing the bulbous section a single time. The enlarged diameter of the bulbous section 10b provides little resistance to squeezing by a technician.

The method of making the above-described pipetting device 10 is described below with reference to FIGS. 4–10. In the example described below, the pipetting device is made from PEBAX 6333. However, it should be recognized by those of ordinary skill in the art that the below-described method may be used to form the pipetting device from a different hydrophilic and elastomeric material such as BAREX or other well known materials.

Figure 5:
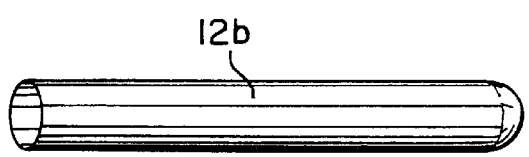
FIG. 5 is a perspective view of the tube material illustrated in FIG. 4 having one end heat sealed.
Figure 4:
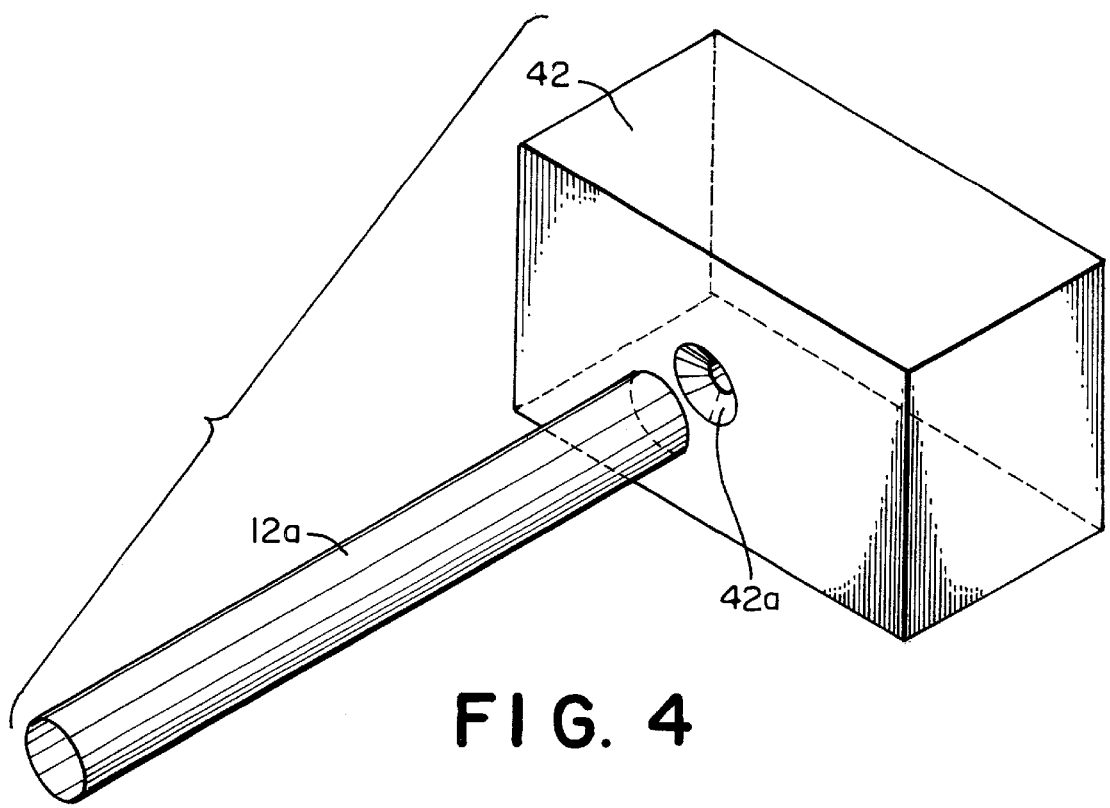
FIG. 4 is a side elevation of a preselected length of tube material and a heat seal die for sealing the end of the tube.

Initially, a preselected length of tube 12a is heat sealed at one end. (Reference numerals 12a, 12b, 12c refer to the configuration of the tube at discrete steps in the formation process of the device) Other sealing methods, such as plugs or adhesives, may be used but are not preferred. Referring to FIG. 4, one end of the tube 12a is contacted with the generally concave depression 42a of a heated die 42. Where PEBAX is used, the temperature of the die 42 is preferably around 375° F. (190.5° C.). At this temperature, the end of the tube segment 12a need only be in contact with the die 42 for one to two seconds to form a heat sealed end as seen in FIG. 5.

Figure 6:
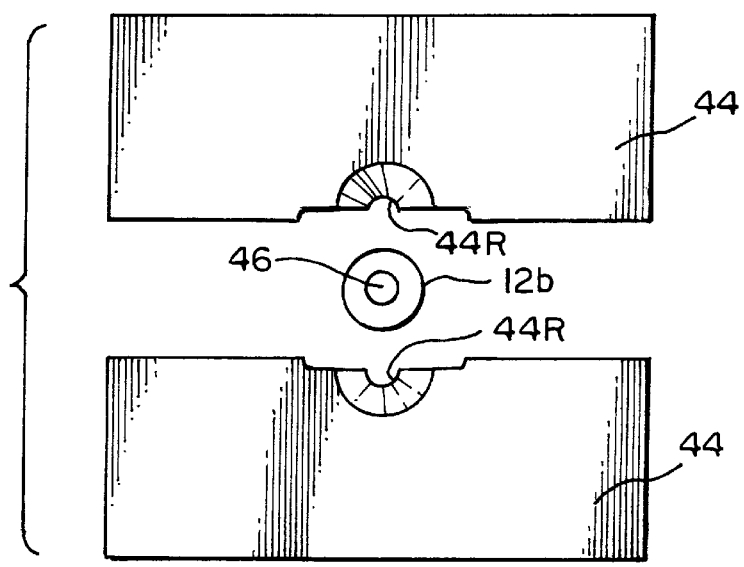
FIG. 6 is an enlarged, front elevation of heated crimping dies and a tube prior to forming the capillary section of the tube.
Figure 7:
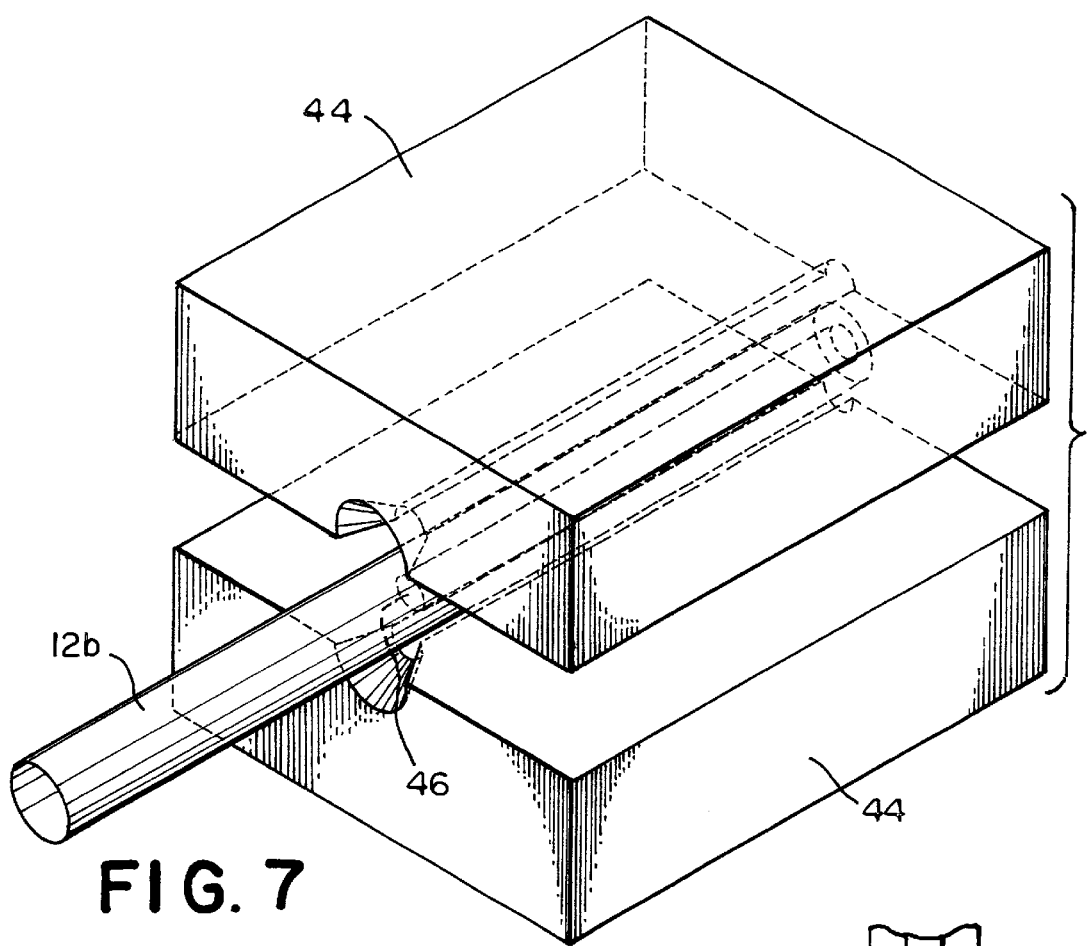
FIG. 7 is an enlarged, perspective view of the heated crimping dies and tube illustrated in FIG. 6.
Figure 8:
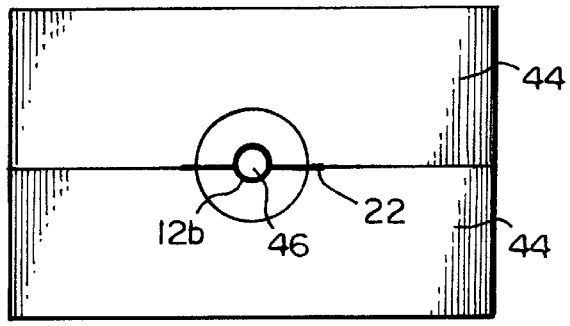
FIG. 8 is an enlarged, front elevation of heated crimping dies after forming the capillary section of the tube.

A selected lengthwise portion (capillary section) of the tube 12b is next reshaped and reduced in diameter with a pair of heated crimping dies 44 as seen in FIGS. 6 and 7. Before the crimping dies 44 contact and squeeze the tube 12b, a cylindrical rod 46 is inserted into the capillary section 10a of the tube 12b. The rod 46 prevents the tube 12b from collapsing and occluding the channel 24a in the capillary section 10a of the tube 12b. The diameter of the rod 46, together with the inner radius 44R of the dies 44, determine the shape and diameter D1 of the channel 24a in the capillary section 10a of the tube 12b. As the dies 44 press and reshape the tube 12b, excess tube material is squeezed radially outwardly from the die, thereby forming the fins 22 as best seen in FIG. 8.

The crimping dies 44 are preferably heated to a temperature of about 325° F. (162.8° C.). At this temperature, the tube 12b need only be in contact with the dies 44 for one to two seconds to reduce the diameter and reshape the tube 12b. Both the end seal die 42 and the crimping dies 44 are preferably made of Teflon coated steel.

Figure 10:
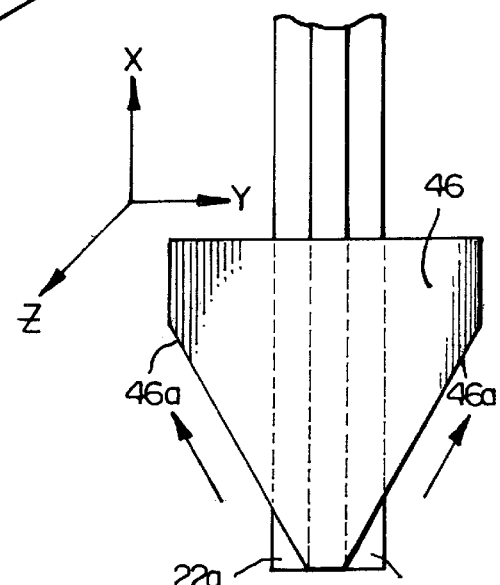
Figure 9:
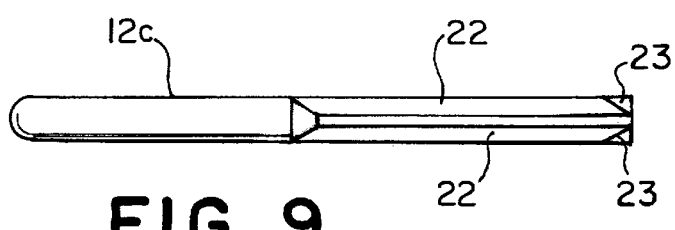
FIG. 9 is a top plan view of the tube after the capillary section has been formed; and, FIG. 10 is fragmentary top plan view of the tube clamped in a shearing die prior to tapering the fins.

After crimping, the tube 12c has the shape shown in FIG. 9. The fins 22 are then sheared or cut (such as along the cut-off lines 23 of FIG. 9) to form the tapered capillary end of the device 10 such as shown in FIGS. 1 and 3. It is preferred to clamp the port end of the tube 12c in a pair of shearing dies 46 such as seen in FIG. 10, and shear the protruding portion 22a of the fins 22 along the tapered portion 46a of the dies 46. Shearing in the longitidinal direction, shown by arrows in the X,Y plane, is preferred since the tube material is very thin and elastomeric. Shearing in the Z plane requires machinery with very low tolerances and is therefore undesirable.

Finally, the vent hole 20 is drilled in the capillary section 10a of the tube. Simultaneously, the location of the vent hole 20 may be marked with ink on the diametrically-opposite side of the tube. Graphics or other identifying indicia may also be printed on the fins.

Table I illustrates a that the calibrated sample volume can be changed by merely changing the vent hole length L3 and/or changing the capillary section diameter D1. The vent hole length is easily changed by repositioning the drill at a different location relative the tube. The capillary section diameter D1 is easily changed by replacing the old rod 46 with a new rod 46 having a different diameter. Thus, the same machinery set up can be easily and quickly reconfigured to produce a batch of pipette devices having a calibrated sample volume different than the previous batch.

The method of the invention also produces a batch of pipette devices having a far more accurate tolerance than the prior art. For example, since the thickness tolerance of extruded stock plastic tubing is large, a capillary tube formed therefrom using blow molding will also have a large tolerance. In the method of the present invention, the stock plastic tubing is reshaped around the rod 46 by the crimping dies 44.

Imperfections inherent in the extrusion process are corrected by the constant fixturing of the rod 46 and dies 44. As a result, the tolerance of the finished pipette device 10 are much lower than blow molded capillary tubes, and are as low as the tolerance of glass capillary tubes.

What is claimed is:

1. A disposable, capillary pipette device for admitting and emitting a fluid sample, said device formed from a single, continuous tube of material comprising:
   a) a single, continuous, tube of hydrophilic and elastomeric material, said tube having a flexible wall and a channel extending from a first end to a second end;
   b) said first end of said tube being open and forming a fluid flow port having a diameter D1 for admitting and emitting liquids to and from the tube;
   c) said second end of said tube being closed and forming a sealed end;
   d) a capillary section formed at the first end of said tube constructed and arranged to admit the liquid sample into said tube, said capillary section having a capillary tube wall extending a distance L1 from said fluid flow port to a preselected intermediate point on said tube, said tube having an inner diameter equal to D1 in said capillary section;
   e) a vent hole extending through said flexible wall in the capillary section of said tube, said vent hole having a diameter D3 smaller than D1, said vent hole being positioned in the tube at a preselected distance from said port to define a liquid sample chamber within said capillary section, said liquid sample chamber having a preselected calibrated volume; and,
   f) a bulbous section formed proximate the second end of said tube, said bulbous section extending a distance L2 from said preselected intermediate point to said sealed end, said tube having an inner diameter D2 greater than D1 in said bulbous section, said bulbous section constructed and arranged to emit the entire volume of liquid sample contained in said capillary section by manually squeezing said bulbous section.

2. The device recited in claim 1, said material comprising a polyether block polyamide.

3. The device recited in claim 1, said material comprising a wettable thermoplastic acrylonitrile barrier.

4. The device recited in claim 1, said tube having a thickness in the range of 5 to 7 mils (0.13 to 0.18 mm.).

5. The device recited in claim 1, said fluid flow port having a diameter D1 in the range of 0.03 to 0.1 in (0.8 to 0.25 cm.).

6. The device recited in claim 1, said seal comprising a heat seal.

7. The device recited in claim 1, said channel having a diameter D2 in the range of 0.15 to 0.3 in. (0.38 to 0.76 cm.).

8. The device recited in claim 1, said vent hole having a diameter in the range of 0.004 to 0.016 in. (0.01 to 0.04 cm.).

9. The device recited in claim 1, wherein D2 is at least two times as large as D1.

10. The device recited in claim 1, wherein D2 is at least three times as large as D1.

11. The device recited in claim 1, said vent hole being located a distance L3 from said port, said liquid sample chamber having a calibrated volume ($\pi(D1/2)^2 L3$) from 5 to 150 microliters.

12. The device recited in claim 11, said calibrated volume being less than the volume of the bulbous section.

13. A disposable, capillary pipette device for admitting and emitting a fluid sample, comprising:
   a) a single, contiguous, tube of hydrophilic and elastomeric material, said tube having a flexible wall and a channel extending from a first end to a second end;
   b) a fluid flow port having a diameter D1 at the first end of the tube for admitting and emitting liquids to and from the tube;
   c) a seal at the second end of the tube to form a sealed end;
   d) a capillary section formed at the first end of said tube constructed and arranged to admit the liquid sample into said tube, said capillary section having a capillary tube wall extending a distance L1 from said fluid flow port to a preselected intermediate point on said tube, said channel having an inner diameter equal to D1 in said capillary section;
   e) a vent hole extending through said flexible wall in the capillary section of said tube, said vent hole having a diameter D3 smaller than D1, said vent hole being positioned in the tube at a preselected distance from said port to define a liquid sample chamber within said capillary section, said liquid sample chamber having a preselected calibrated volume; and,
   f) a bulbous section formed proximate the second end of said tube, said bulbous section extending a distance L2 from said preselected intermediate point to said seal, said channel having an inner diameter D2 greater than D1 in said bulbous section, said bulbous section constructed and arranged to emit the entire volume of liquid sample contained in said capillary section by manually squeezing said bulbous section,
   including a pair of opposed fins fixed to and projecting radially-outwardly from said capillary section, said fins extending along said capillary section.

14. The device recited in claim 13, including identifying indicia printed on said fins.

15. A disposable, preselected-volume, capillary pipette device, comprising:
   a) a single, contiguous, tube of hydrophilic and elastomeric material, said tube having a flexible wall and a channel extending from a first end to a second end;
   b) a fluid flow port having a diameter D1 at the first end of the tube for admitting and emitting liquids to and from the tube;
   c) a seal at the second end of the tube;
   d) a capillary section formed at the first end of said tube, said capillary section extending a distance L1 from said fluid flow port to a preselected intermediate point on said tube, said channel having an inner diameter equal to D1 in said capillary section;
   e) a bulbous section formed proximate the second end of said tube, said bulbous section extending a distance L2 from said preselected intermediate point to said seal, said channel having an inner diameter D2 greater than D1 in said bulbous section; and
   f) a vent hole extending through said flexible wall in the capillary section of said tube, said vent hole having a diameter D3 smaller than D1, said vent hole being positioned in the tube at a preselected distance from said port to define a liquid sample chamber within said capillary section, said liquid sample chamber having a preselected calibrated volume,
   said material comprising a polyether block polyamide or a wettable thermoplastic acrylonitrile barrier;
   said tube having a thickness in the range of 5 to 7 mils (0.13 to 0.18 mm);
   said fluid flow port having a diameter D1 in the range of 0.03 to 0.1 in. (0.08 to 0.25 cm.);
   said seal comprising a heat seal;
   said channel having a diameter D2 in the range of 0.15 to 0.3 in. (0.38 to 0.76 cm.);
   said vent hole having a diameter in the range of 0.004 to 0.016 in. (0.01 to 0.04 cm.);

wherein D2 is at least two times as large as D1;

wherein D2 is at least three times as large as D1;

said vent hole being located a distance L3 from said port, said liquid sample chamber having a calibrated volume ($\pi(D1/2)^2 L3$) from 5 to 150 microliters;

said calibrated volume being less than the volume of the bulbous section;

including a pair of opposed fins fixed to and projecting radially-outwardly from said capillary section, said fins extending along said capillary section.

16. A method of preparing a liquid sample for testing, comprising the steps of:
   a) providing a disposable, preselected-volume, capillary pipette device, said device formed from a single, continuous tube of material, comprising:
      i) a single, continuous, tube of hydrophilic and elastomeric material, said tube having a flexible wall and a channel extending from a first end to a second end;
      ii) said first end of said tube being open and forming a fluid flow port having a diameter D1 for admitting and emitting liquids to and from the tube;
      iii) said second end of said tube being closed and forming a sealed end;
      iv) a capillary section formed at the first end of said tube, said capillary section extending a distance L1 from said fluid flow port to a preselected intermediate point on said tube, said tube having an inner diameter equal to D1 in said capillary section;
      v) a bulbous section formed proximate the second end of said tube, said bulbous section extending a distance L2 from said preselected intermediate point to said sealed end, said tube having an inner diameter D2 greater than D1 in said bulbous section; and
      vi) a vent hole extending through said flexible wall in the capillary section of said tube, said vent hole having a diameter D3 smaller than D1, said vent hole being positioned in the tube at a preselected distance from said port to define a liquid sample chamber within said capillary section, said liquid sample chamber having a preselected calibrated volume;
   b) contacting the port end of the device to a source of liquid;
   c) admitting a preselected, calibrated volume of liquid to said device by capillary action;
   d) emitting the volume of liquid from said device by squeezing the bulbous section of the device.

17. A disposable, capillary pipette device for admitting and emitting a fluid sample, said device being formed from a single, continuous tube of material, comprising:
   a) a single, continuous tube of hydrophilic and elastomeric material, said tube having a flexible wall and a channel extending from a first end to a second end;
   b) said first end of said tube being open and forming a fluid flow port having a diameter D1 for admitting and emitting liquids to and from the tube;
   c) said second end of said tube being closed and forming a sealed end;
   d) a capillary section formed at the first end of said tube, said capillary section having a capillary tube wall extending a distance L1 from said fluid flow port to a preselected intermediate point on said tube, said capillary section being formed by crimping said tube along said capillary section to reduce the diameter of the channel in said capillary section;
   e) a vent hole extending through said flexible wall in the capillary section of said tube, said vent hole being positioned in the tube at a preselected distance from said port to define a liquid sample chamber within said capillary section, said liquid sample chamber having a preselected calibrated volume;
   f) a bulbous section formed proximate the second end of said tube, said bulbous section extending a distance L2 from said preselected intermediate point to said sealed end, said tube having an inner diameter D2 greater than D1 in said bulbous section, said bulbous section emitting the entire volume of liquid sample contained in said capillary section by manually squeezing said bulbous section.

* * * * *